United States Patent [19]
Leying et al.

[11] Patent Number: 6,027,886
[45] Date of Patent: *Feb. 22, 2000

[54] METHOD FOR THE QUANTITATIVE DETECTION OF SPECIFIC NUCLEIC ACID SEQUENCES

[75] Inventors: Hermann Leying, Bichl; Matthias Hinzpeter, München; Heiko Wittor, Tutzing; Hans-Peter Fritton, Mörlenbach, all of Germany

[73] Assignee: Roche Diagnostics GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/771,781

[22] Filed: Dec. 20, 1996

[30] Foreign Application Priority Data

Dec. 23, 1995 [DE] Germany ............................ 195 48 680

[51] Int. Cl.⁷ ...................................................... C12Q 1/68
[52] U.S. Cl. ................................................................ 435/6
[58] Field of Search ............................. 435/6, 91.1, 91.2, 435/196, 199; 436/501; 536/23.1, 24.1, 24.3, 24.31, 24.32, 25.32, 24.33; 935/77, 78

[56] References Cited

U.S. PATENT DOCUMENTS

| | | | |
|---|---|---|---|
| 4,946,773 | 8/1990 | Maniatis et al. .............................. | 435/6 |
| 4,988,617 | 1/1991 | Landegren et al. .......................... | 435/6 |
| 5,200,313 | 4/1993 | Carrico ........................................ | 435/6 |
| 5,210,015 | 5/1993 | Gelfand et al. .............................. | 435/6 |
| 5,220,313 | 6/1993 | Carrico ........................................ | 435/6 |
| 5,491,063 | 2/1996 | Fisher et al. ................................. | 435/6 |

FOREIGN PATENT DOCUMENTS

| | | |
|---|---|---|
| 0 127 327 | 12/1984 | European Pat. Off. . |
| 0 437 774 | 7/1991 | European Pat. Off. . |
| 0 523 557 | 1/1993 | European Pat. Off. . |
| 0 742 286 | 11/1996 | European Pat. Off. . |
| 0 754 763 | 1/1997 | European Pat. Off. . |
| 2 737 502 | 2/1997 | France . |
| WO 90/12116 | 10/1990 | WIPO . |
| WO 92/07093 | 4/1992 | WIPO . |
| WO 96/21743 | 7/1996 | WIPO . |

OTHER PUBLICATIONS

Ralf Sommer and Diethard Tautz, "Minimal homology requirements for PCR priemrs," Nucleic Acids Research, vol. 17, No. 16, p. 6749, 1989.

Ambion 1996 Catalog, pp. 1, 73–76, 1995.

Haines et al., "RNA Abundance Measured by a Lysate RNase Protection Assay," Bio Techniques 12(5):736–741, 1992.

Chan et al., "Nonisotopic Quantitation of mRNA Using a Novel RNase Protection Assay: Measurement of erbB–2 mRNA in Tumor Cell Lines," Analytical Biochemistry 242:214–220, Nov. 15, 1996.

*Primary Examiner*—Kenneth R. Horlick
*Assistant Examiner*—Janell E. Taylor
*Attorney, Agent, or Firm*—Nikaido Marmelstein Murray & Oram, LLP.

[57] ABSTRACT

Method and kit for the quantitative detection of specific oligonucleotide or polynucleotide sequences which is characterized in that a sample mixture containing RNA or single-stranded DNA is hybridized with an oligonucleotide or polynucleotide probe(s) which are complementary to the nucleotide sequence to be determined and carry(ies) a specificplly bindable and a detectable chemical group subsequently it is admixed with an agent that cleaves single-stranded polynucleotide sequences and the immobilized or non-immobilized nucleotide probe is determined after transfer into a suitable reaction vessel. It has proven to be particularly advantageous when a mixture is used which is composed of different cleaving reagents.

36 Claims, 3 Drawing Sheets

RIBONUCLEASE PROTECTION ELISA

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 41 base pairs
       (B) TYPE: nucleotide
       (C) STRANDEDNESS: single
       (D) TOPOLOGY: linear (ii) MOLECULE TYPE: nucleic acid (xi) SEQUENCE DESCRIPTION: SEQ ID NO:1:

GGATCCTAAT ACGACTCACT ATAGGGAGGC GAGATTTTCA G                    41

(2) INFORMATION FOR SEQ ID NO:2:

(i) SEQUENCE CHARACTERISTICS:
       (A) LENGTH: 30 base pairs
       (B) TYPE: nucleotide
       (C) STRANDEDNESS: single
       (D) TOPOLOGY: linear (ii) MOLECULE TYPE: nucleic acid (xi) SEQUENCE DESCRIPTION: SEQ ID NO:2:

TTTTTTTTTT TTTTTTTTTT CAGGCGTAGC                                 30

METHOD FOR THE QUANTITATIVE DETECTION OF SPECIFIC NUCLEIC ACID SEQUENCES

The invention describes a method for the detection and for the quantitative determination of specific oligonucleotide or polynucleotide sequences which is essentially characterized in that a single-stranded or double-stranded nucleic acid in particular mRNA present in a mixture such as e.g. a biological sample is hybridized in solution with an oligonucleotide or polynucleotide sequence which is essentially complementary to the sequence to be determined, is treated with an agent which cleaves preferably single-stranded oligonucleotide or polynucleotide sequences, it is subsequently immobilized on a solid phase and the amount of bound hybrid is determined. It has proven to be particularly suitable when the cleavage reagent is a mixture of two different RNases and the binding to the solid phase is achieved by means of a specifically bindable chemical group coupled to the complementary nucleotide sequence(s) and the detection is carried out by means of a second chemical group.

A number of methods are nowadays known for the detection of nucleic acids. These are usually based on the principle of hybridization and in most cases the sequence to be determined is firstly immobilized on a solid phase and subsequently a labelled nucleic acid probe is added. However, the method is time-consuming and cannot easily be carried out successfully by an unskilled practition. This is in particular due to the fact that hybridization on a solid phase proceeds less efficiently.

Alternatively nucleic acids can be determined via the in situ labelling of the sample nucleic acid and immobilization on a solid phase which is mediated by a sequence-specific nucleotide sequence probe. In another method two sequence-specific probes for the nucleic acid to be determined are used. The in situ labelling as well as the hybridization with two probes on a solid phase often do not proceed reproducibly i.e. are difficult to quantify or only with a high inaccuracy, moreover they are experimentally complicated and hence less suitable for routine clinical diagnostics. Corresponding methods and variants are known as Northern blot methods, nuclease protection assays and quantitative RT-PCR methods and are today among the standard methods for quantifying nucleic acids (T. Maniatis, Molecular Cloning: A Laboratory Manual, 2nd ed. (1989); R. E. Farell, RNA Modologies: A Laboratory Guide for Isolation and Characterisation, Academic Press; J. W. Larrick, Trends Biotechnol. 10, 146–152 ('992); E. S. Kawasaki, A Guide to Methods and Applications (eds. Innis, M. A. et al) Academic Press). A disadvantage of the Northern blot method and the quantitative RT-PCR is that it is imperative to start with isolated RNA. In the case of the blotting methods in particular the nucleic acid transfer and the immobilization of the nucleic acid are incomplete. In the classical nuclease protection assay it is in addition necessary to inactivate the nucleases by protease digestion.

In addition it is known that nucleic acids and in particular single-stranded nucleic acids such as e.g. mRNA can be detected in the so-called microtitre plate method in which the hybridization reaction is carried out in solution. In this method the hybridization is usually carried out with a biotin-labelled cDNA probe. The nucleic acid hybrids are subsequently immobilized via the biotin label and detected for example in a conventional ELISA assay using an antibody which specifically binds DNA/RNA hybrids (F. Coutlee et al. J. Biol. Chem. 256, 11601–11604 (1990); EP 0 336 454 etc.).

However, a disadvantage of this method is that it is time-consuming and in the first case only DNA can be used as a capture probe. This is due to the fact that the detection is via DNA/RNA-specific antibodies. In addition the systems are less sensitive.

Also a recently published method in which RNA is firstly hybridized with a capture probe that is already immobilized in a microtitre plate well and subsequently labelled with a fluorescent intercalating agent and detected (T. Okamoto et al., Anal. Biochem. 221, 202–204 (1994)), only partially overcomes the disadvantages. Depending on the length of the capture probe this method leads to high background signals since not only the actual RNA to be detected but also the immobilized capture probe is labelled.

Therefore the object of the present invention is to provide a method for the determination of a specific oligonucleotide or polynucleotide sequence which overcomes the disadvantages of the methods described in the state of the art i.e. in particular it is easy to carry out and can be automated, it can be carried out without a prior RNA isolation (in cell lysates) and can quantitatively detect nucleic acids and moreover is characterized by low background signals.

The object is achieved by a method for the determination of a specific oligonucleotide or polynucleotide sequence in a sample mixture which comprises the following steps:

- Combining a sample mixture containing RNA or single-stranded DNA with a lysis or hybridization buffer,
- contacting the homogenized sample solution with one or several, preferably two oligonucleotide or polynucleotide probe(s) or appropriate derivatives, in particular peptide derivatives, which are essentially complementary to the oligonucleotide or polynucleotide sequence to be determined in which at least two different labelling residues are bound to the same probe or to two or several different probes,
- hybridizing under stringent conditions at a temperature of approximately 30° to 80° C. and within ca. 10 minutes to 15 hours,
- diluting the mixture obtained with a suitable buffer and adding an agent that preferably cleaves single-stranded oligonucleotide or polynucleotide sequences into mononucleotides or oligonucleotides,
- transferring the mixture into a reaction vessel or into a reaction well the inside of which is coated with a substance which binds at least one of the bound labelling residues,
- immobilizing the oligonucleotide or polynucleotide hybrid modified with two different labelling groups or one labelling group on the solid phase and subsequently washing and
- detecting the immobilized labelled oligonucleotide or polynucleotide probe or the non-immobilized labelled nucleotide probe, the detection being carried out directly or for example by means of a suitable enzyme-labelled antibody.

The complementary oligonucleotide or polynucleotide sequence i.e. the probe sequence is linked to at least two different labelling residues one of which is a specifically bindable chemical group and the other residue(s) is/are any desired detectable chemical group(s). In this case the oligonucleic acid or polynucleic acid hybrid that is later immobilized via a labelling group is detected. However, it is also possible to use several complementary probe sequences in the method according to the invention. In such a case one of the probe sequences carries a specifically bindable group and at least one other specific probe sequence carries one or several groups that can be determined. In this analogous embodiment the specific nucleic acid hybrid that is located in solution is detected. In both variants it is then possible to deduce the amount of specific nucleic acid in a particular sample volume. Biotin, iminobiotin, avidin or other streptavidin binding molecules or haptens such as for example digoxigenin have proven to be advantageous as immobilizable, i.e. specifically bindable, chemical groups. These and other bindable residues are known to a person skilled in the art.

For the labelling of the complementary probe sequence/probe sequences enzymatically active groups that can be determined or detected come into consideration such as for example peroxidase, alkaline phosphatase or β-galactosidase, or fluorescent groups such as fluorescein or appropriate derivatives, chromophores or luminescent groups of various types or detectable haptens such as for example digoxigenin. These chemical groups can be incorporated into the nucleic acid by chemical or enzymatic means. Radioisotopes have, however, also proven to be suitable which are for example incorporated in the presence of a terminal transferase or T4 RNA ligase and an appropriately labelled nucleotide or oligonucleotide.

In addition a process can be used for introducing non-radioactively labelled deoxynucleotides into nucleic acids or RNA molecules which contain at least one deoxynucleotide at their 3' end which carries a non-radioactive labelling group. An appropriate process is described in the European Patent Application file number 95 102 669.9.

It has proven to be particularly advantageous when the complementary oligonucleotide or polynucleotide is labelled with an appropriate hapten such as for example biotin or digoxigenin which is complexed in a compound containing platinum such as for example {Pt(ethylenediamine) (Me$_2$SO) (hapten-NH (CS) NHCH$_3$}. An appropriately activated form of such platinum complexes is used for the labelling. Such platinum compounds are usually referred to as a "universal linkage system" (ULS) (EP 0 539 466/WO 92/01699).

The ratio of detection to binding label is unproblematic in most cases. However, it has proven to be advantageous when the binding label is present in a substoichiometric amount; a ratio of detection to binding label of 10 to 1 is particularly advantageous.

A further preferred embodiment of the invention is to use a peptide nucleic acid derivative with a base sequence that is essentially complementary to the sequence to be determined instead of a labelled complementary oligonucleotide or polynucleotide probe.

This means that all types of probes of any desired length can be used for the hybridization in particular antisense RNA and so-called "peptide nucleic acid" (PNA) i.e. nucleic acids with a peptide backbone. This is of importance since hybridization between PNA and RNA molecules is more efficient than between pure RNA molecules and these in turn hybridize more efficiently than DNA and RNA molecules. The length of the specific probes is unproblematic. As a rule probes with lengths of ca. 10 to 8000 nucleotides are used, preferably they are 100 to 1000mers and often oligonucleotides or polynucleotides composed of ca. 100 nucleotides are adequate.

Apart from pure nucleic acid fractions such as in particular mRNA fractions, natural or artificial mixtures of total RNA (rRNA, tRNA, mRNA) and also fractions (cell lysates) obtained from cell cultures as well as tissue cell extracts and tissue homogenates as well as blood of human or animal origin as well as plant extracts come into consideration as the sample material to be analysed.

Suitable lysis and hybridization buffers are based on buffer substances which have a good buffering capacity in the pH range of ca. 2 to 10, preferably between pH 7.0 and 8.5. Corresponding buffer substances are for example Tris-HCl, HEPES, MOPS or Tris-borate.

Furthermore the buffers suitable for the method according to the invention can contain a disulfide reducing reagent such as e.g. dithioerythritol, dithiothreitol, mercaptoethanol preferably at a concentration of 0.01 to 1% (w/v). In addition it has proven to be advantageous for the buffer system to contain a denaturing substance such as detergents at relatively high concentrations. In this case dodecylsulfate salts or appropriate derivatives at a concentration of 0.1 to 15% (w/v) as well as, particularly when RNase-rich tissue is used, salts of the guanidinium thiocyanate (GTC) type or appropriate derivatives and namely in a concentration range of ca. 1 to 7 M have proven to be particularly suitable. In this connection it has turned out that it is of particular advantage if the solutions for the determinations are almost free of RNase activity. This means that a maximum of 5% residual activity of RNase may be present.

The buffer systems that can be used for the method according to the invention can in addition contain further salts such as e.g. lithium chloride or other auxiliary agents. Moreover it has proven to be advantageous when an RNase inhibitor such as e.g. one obtained from placenta is also present and/or the buffer solution is previously sterilized or decontaminated with dimethyldicarbonate or diethylpyrocarbonate.

The hybridization is carried out under stringent conditions after an optional denaturation (see e.g. Analyt. Biochem. 163, 281–291 (1987)). In this case temperatures between 30° and 80° C. and the addition of GTC, preferably at a concentration of 4 M, have proven to be particularly suitable. The time can be varied in a wide range (ca. 10 minutes to 24 hours) i.e. it is not critical. In many cases an incubation period of 4 to 12 hours has proven to be ideal.

After the hybridization the sample mixture in which the specific hybrid as well as single-stranded non-hybridized nucleic acids are located is diluted with a suitable buffer such as e.g. so-called RNase digestion buffer (e.g. Tris-HCl/EDTA/sodium acetate, pH 7.5). Dilutions of 1:2 to 1:100, in particular a ratio of 1:10 to 1:20, have proven in this case to be particularly suitable.

Subsequently an agent is added to the mixture which preferably cleaves single-stranded i.e. non-hybridized nucleic acid sequences into mononucleotides or oligonucleotides at a final concentration of ca. 0.01 U/ml to 50,000 U/ml preferably of ca. 0.05 to 20,000 U/ml. RNases which especially come into consideration are RNase A, RNase T1 or RNase I or corresponding mixtures of these enzymes. In this case mixtures composed of different cleaving agents have proven to be particularly preferable. In particular mixtures in which one type of cleavage agent is present in only a fraction of the amount the other cleavage agent(s) have proven to be especially suitable. The fraction can be between 1/5 to a maximum of 1/100,000 of the total amount of cleavage agent. Advantageous concentration ranges for the various cleavage agents are for example: 0.01 to 10,000 U/ml RNase A, 0.05 to 50,000 U/ml RNase T1 or 0.1 to 10 U/ml RNase I, in each case relative to the final volume.

As a rule several minutes are adequate for the digestion reaction; however, an incubation period of several hours has not proven to be detrimental. In this case an incubation period of ca. 2 minutes to ca. 3 hours and a temperature range of 20° to 50° C. has proven to be particularly preferable. In many cases a temperature of ca. 37° C. was ideal and usually the required temperatures were not below ca. 10° C. and not above ca. 80° C.

The mixture is subsequently transferred into a separate reaction vessel. The reaction vessel is composed of a coated solid phase, the solid phase being composed in principle of a series of materials and shapes such as e.g. microparticles so-called beads, pore-containing or non-permeable membranes, the inner surfaces of reaction vessels such as test tubes or microtitre plates. The present invention is preferably carried out in coated microtitre plates especially those which have been coated with streptavidin (SA) or avidin. Appropriate measures and solid phases are known to a person skilled in the art and are described for example in EP 0344578.

The immobilization of the labelled nucleic acid hybrid takes at least ca. 30 seconds; several hours i.e. also overnight do not worsen the result. As a rule 2 to 10 minutes are adequate; ca. 5 minutes at a temperature of ca. 37° C. is preferred. Depending on the length of the incubation period temperatures of 4° to 80° C. are, however, also suitable.

It is of great importance to thoroughly wash after conclusion of the immobilization process in order for example to remove as quantitatively as possible non-specifically bound labelled nucleic acid hybrids or labelled single-stranded RNA/DNA as well as the reagents cleaving the nucleic acids.

The subsequent detection of the immobilized nucleic acid hybrid is either carried out directly via the detectable residue bound to the hybrid which for example can be a chemiluminescent or fluorescent dye or can be carried out indirectly if the detectable residue is a hapten such as digoxigenin (DIG). In such a case the incubation is for example carried out with POD-labelled <DIG> antibody for ca. 30 to 60 minutes at ca. 37° C. and 400 rpm. The subsequent detection is achieved for example by pipetting in a substrate solution such as for example luminol/iodophenol or tetramethylbenzidine and measuring the absorbance signal after ca. 3 to 30 minutes.

The kit for the detection or the determination of single-stranded specific oligonucleotide or polynucleotide sequences is composed of at least three of the following components:

(a) lysis or hybridization buffer, (b) at least one labelled oligonucleotide or polynucleotide probe that is complementary to the polynucleotide sequence to be determined, (c) an agent cleaving single-stranded poly-nucleotide sequences into mononucleotides and oligonucleotides as well as a suitable dilution buffer, (d) an enzyme-labelled antibody which is directed against the labelling group of the oligonucleotide or polynucleotide probe which is complementary to the polynucleotide sequence to be determined, as well as a suitable substrate for the enzyme and (e) a reaction vessel the inside of which is coated with a substance which can bind to a second labelling group of the oligonucleotide or polynucleotide probe that is complementary to the polynucleotide sequence to be determined.

A kit has proven to be particularly suitable which contains three of the five said components such as the components a, b and d or the components a, d and e.

A kit has also proven to be particularly suitable which contains four of the five said components such as the components a, b, d and e or the components a, c, d and e.

Above all a kit has proven to be particularly suitable which contains all five said components.

Moreover a kit has proven to be particularly suitable which contains as the agent cleaving single-stranded polynucleotide sequences a mixture of different cleaving agents such as RNase T1 and RNase A. It has proven to be especially advantageous according to the invention when the amount of one of the cleaving agents present in the mixture is only a fraction of that of the other cleaving agent(s). The fraction can be $1/5$ to a maximum of $1/100,000$ of the total amount of cleaving agents.

The method according to the invention has the special advantage of higher sensitivity since surprisingly it was possible to reduce interfering background signals, the simplicity of the experimental procedure (no RNA isolation is absolutely necessary, no blotting steps are required) and ability to automate.

In addition an advantage of the method according to the invention is that the hybridization reaction is not carried out on a solid phase but rather in solution. Hybridizations in solution are more efficient and considerably faster.

Figure legends:

FIG. 1:

Shows the result of example 1 in which =+CAT a gene which does not occur endogenously in eukaryotic cells, the filled symbols denote "−CAT RNA". 6.7 ng CAT RNA was applied per reaction well and could be detected at a signal/noise ratio of >15.

The left signals are due to digestion with RNase T1, the right signals are due to a mixtur of RNase T1/RNase A. In the former case unspecific hybrids cannot be completely removed even by increasing the RNase T1 concentration; in contrast the mixture composed of RNase T1 and RNase A leads to a further considerable improvement even at low concentrations of RNase A.

FIG. 2:

Shows the result of example 2 in which =actin and =CAT.

FIG. 3:

Shows a flow diagram of the method according to the invention.

The invention is elucidated by the following examples:

Introduction

The method according to the invention serves to detect and to quantify specific RNA and to analyse gene and mRNA structures.

The technique is based on the hybridization of e.g. a bio/DIG labelled antisense RNA probe with the RNA pool to be tested (sample material). Complementary parts of the test RNA and the probe form hybrids. Non-hybridized target and probe RNAs are digested by means of RNases, the hybrids remain intact. The hybrids are bound in the streptavidin coated microtitre plate via the biotin label and detected in this case by means of <DIG> POD.

The bio/DIG labelled antisense RNA probe is obtained by in vitro transcription of chloramphenicol acetyl transferase (CAT) PCR fragments which were provided with the T7 polymerase promoter using appropriate primers.

In the following examples the measurement of CAT-specific RNA in a matrix of yeast total RNA by means of ribonuclease protection ELISA (RPE) is described.

EXAMPLE 1

The transcription vector construct for producing the CAT antisense RNA probe and the specific CAT-RNA for contacting with the samples are obtained from the Ambion Company. Other reagents for producing the probes are obtained from Boehringer Mannheim. Yeast total RNA (c=5 mg/ml), hybridization buffer (40 mM Pipes, 400 mM NaCl, 1 mM EDTA, 80% deionized formamide, pH 6.4), RNase digestion buffer (10 mM Tris-HCl, 5 mM EDTA, 300 mM NaOAc, pH 7.5), RNase A (3.5 mg/ml), RNase T1 (10 U/µl) were used from a ribonuclease protection kit (gel format, Boehringer Mannheim).

All further reagents such as the streptavidin coated microtitre plate (MTP), <DIG>POD-antibody, RNase-free conjugate dilution buffer (40 mM $KPO_4$, 1 mM EDTA, 0.25% BSA, pH 6.8) luminol/iodophenol chemiluminescent substrate and others are obtained from Boehringer Mannheim. Chemiluminescence measurements were carried out using the microplate luminometer LP 96P from Berthold.

Ca. 20 µg CAT-antisense RNA are obtained using 1 µg template DNA in each case according to the manufacturer's instructions by means of the DIG RNA labelling kit (Boehringer Mannheim) and by appropriate replacement of UTP by bio-UTP (molar ration UTP/DIG-UTP=3/1 and UTP/bio-UTP=20/1). After ethanol precipitation and resuspension in 60 µl TE in each case it was stored at −70° C.

30 µl hybridization buffer and 2 µl yeast total RNA solution (10 µg) were each pipetted into six sterile Eppendorf vessels (on ice). 0.5 µl CAT-RNA (50 ng/µl) was added to mixtures 1–3. The bio/DIG labelled CAT-RNA probe was diluted with TE to ca. 30 ng/µl and 0.5 µl (15 ng) probe was added by pipette to all mixtures. After denaturing for 5 minutes at 90° C., they were hybridized for 4.5 hours at 45° C. and subsequently cooled to 20° C. 350 µl RNase digestion buffer was added by pipette to each mixture and each was subsequently admixed with RNases as follows: 3.5 µl RNase T1 added to mixtures 1 and 4, 38.5 µl RNase T1 added to mixtures 2 and 5, 3.5 µl RNase T1 and 1 µl RNase A (prediluted 1:20 in RNase digestion buffer) was added to each of mixtures 3 and 6. The RNase digestion was carried out for ca. 30 minutes at 30° C. and they were subsequently placed on ice. 100 µl mixture in each case was pipetted into a SA-MTP preheated to 37° C. 5 Minutes binding at 400 rpm. Subsequently they were decanted and washed eight times with 0.1×SSC. 100 µl <DIG>POD conjugate (25 mU/ml) was added by pipette and they were incubated for 30 minutes at 400 rpm and 37° C. Subsequently they were decanted and washed three times with 0.1×SSC. 150 µl luminol/iodophenol was added to each by pipette and they were measured after 3 minutes (integration period 1 second).

| Mixture No. | Relative light intensities |
| --- | --- |
| 1 | 1228767 |
| 2 | 1195821 |
| 3 | 1023721 |
| 4 | 343837 |
| 5 | 260948 |
| 6 | 66162 |

EXAMPLE 2

Synthetic polyadenylated full length CAT sense RNA was prepared as follows:

Synthesis of the template for the in vitro transcription:
The primers CAT up 5'GGA TCC TAA TAC GAC TCA CTA TAG GGA GGC GAG ATT TTC AG 3' (SEQ ID NO.1) and CAT down 5' TTT TTT TTT TTT TTT TTC AGG CGT AGC 3' (SEQ ID NO.2) were used with the plasmid PCATCON (Promega) as a template in a standard PCR (annealing temperature: 50.0° C., reagents from Boehringer Mannheim) to synthesize a DNA with an attached T7 RNA polymerase promoter and poly A/T tail.

in vitro transcription:
100 µl Amplicon was precipitated with 100% ethanol, washed with 70% ethanol and resuspended in 4 µl TE pH 8. 1 µl of this solution was used in a 40 µl in vitro transcription mixture (DIG RNA labelling kit (Boehringer Mannheim) without BIO/DIG incorporation) as a template for RNA synthesis. After ethanol precipitation the concentration of the synthetic CAT sense RNA was estimated as ca. 8 ng/µl by means of the Gibco/DNA mass ladder.

The BIO/DIG labelled antisense RNA probes for actin (800 b) and CAT (241 b) were synthesized and quantified in the same manner (see also example 1).

Ribonuclease protection ELISA:
Recovery of CAT sense RNA in a cell lysate matrix. $10^7$ cells of the cell line K562 were lysed in 1 ml hybridization buffer and the DNA was sheared by passing it several times through a fine cannula. 2 times 5 aliquots were pipetted into sterile Eppendorf cups.

A log 10 dilution series of the above CAT sense RNA was prepared in hybridization buffer (1:10/1:100/1:1000/1:10,000). 2 cups each of cell lysate were mixed with 1 µl in each case of CAT sense RNA at various concentrations (starting at 800 pg/µl) and the two last cups were contacted with 1 µl hybridization buffer in each case.

Ca. 150 pg BIO/DIG labelled antisense RNA probes were pipetted into the lysates that had been brought into contact, hybridized while shaking for 4 hours at 55° C. and filled up to the 11-fold volume with RNase digestion buffer. Subsequently it was digested with 1.28 U/ml RNase A and 514 U/ml RNase T1 (final concentration) for 40 min at 40° C. 100 µl of each was transferred by pipette into a SA-MTP preheated to 50° C. and bound for 5 min. at 500 rpm. Subsequently it was decanted and washed 8 times with 0.1×SSC. The detection was carried out with anti-DIG POD as in example 1 and BM Blue (Boehringer Mannheim) as the substrate (100 µl per well, stopped with 25 µl 1 M sulfuric acid after 6 min, measurement at 450 nm).

Figure 1:
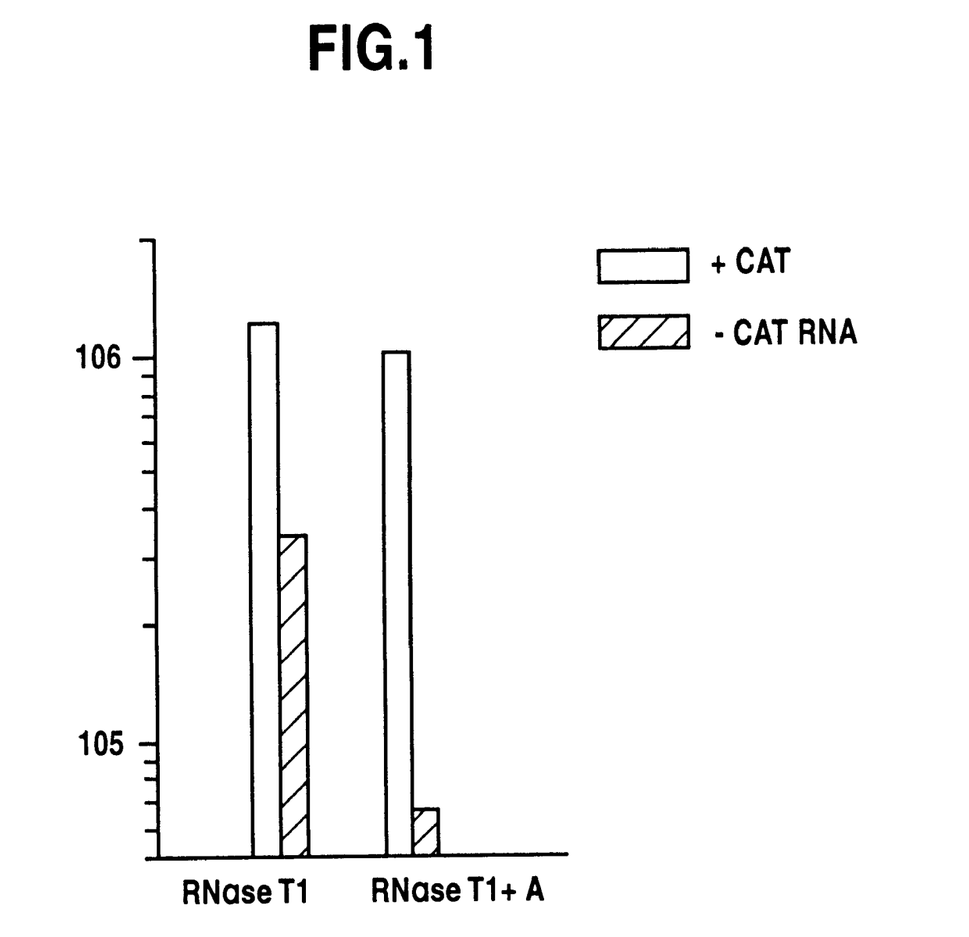
Figure 2:
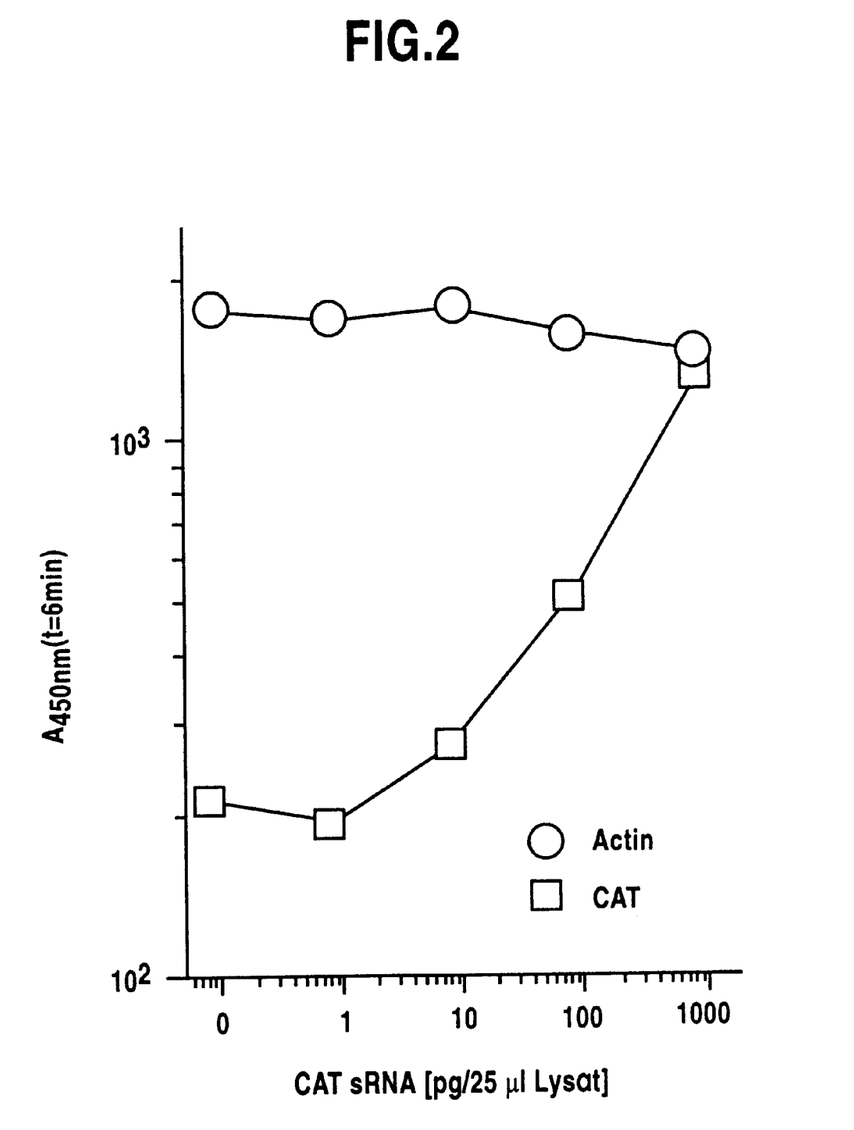
Figure 3:
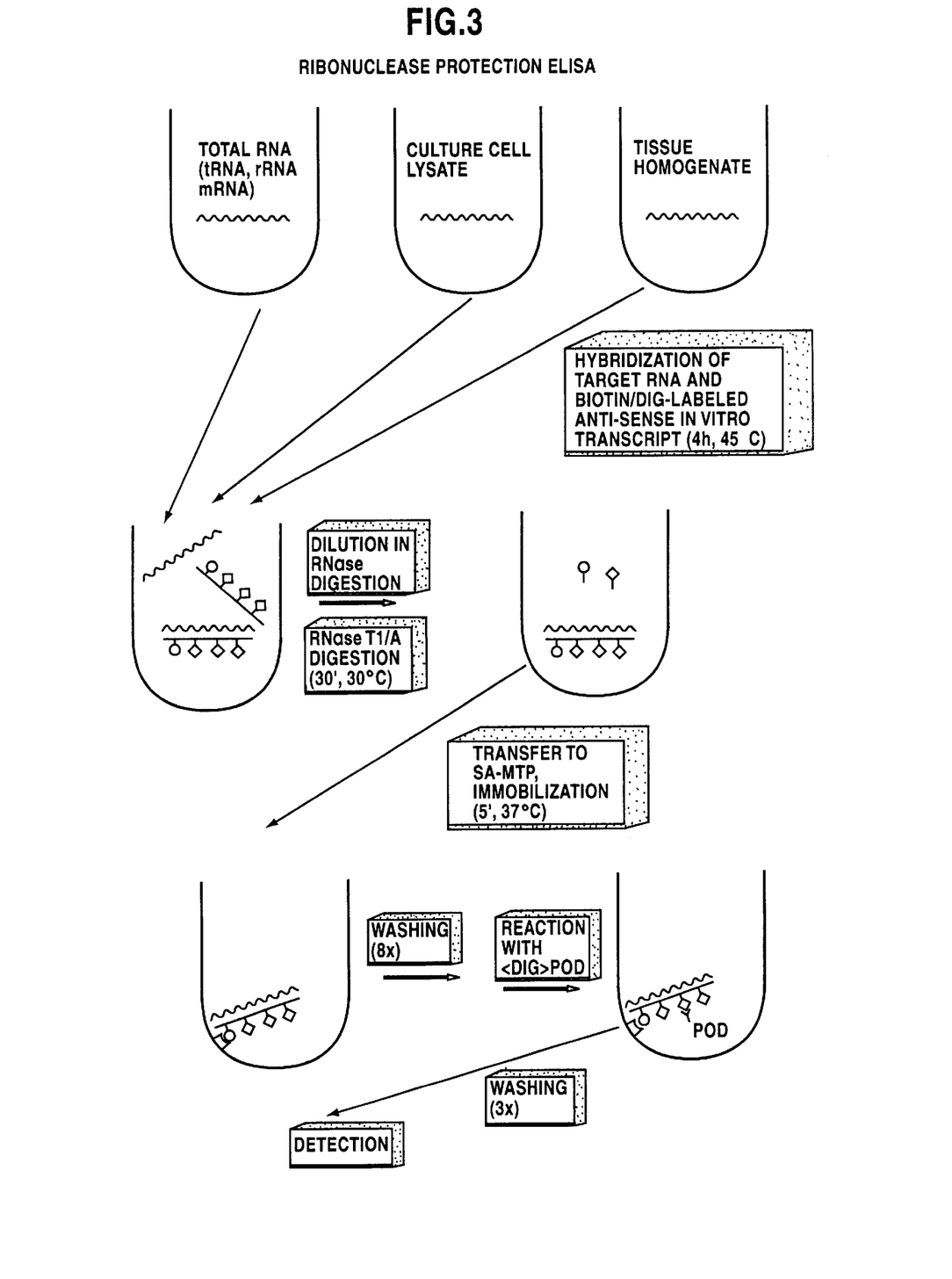

Result:
Various amounts of CAT-sense RNA were detected in a matrix of a cell lysate down to a concentration of less than 10 ng/µl (FIG. 2).

The detected actin transcript concentrations remained as expected constant from aliquot to aliquot.

When contacted with an amount of CAT sense RNA which corresponded approximately to the expected amount of actin sense RNA containing lysate, the signals obtained are of the same magnitude for the both transcripts.

As used in this application, the term "essentially complementary" means that the polynucleotide sequence contains enough complementary sequences compared to its target sequence such that the polynucleotide sequence hybridizes to its target sequence under stringent conditions. Usually, it will be sufficient if the polynucleotide sequence is at least 80% complementary to its target sequence. However, it is preferred that the polynucleotide sequence be at least 90% complementary to its target sequence, and most preferred if the polynucleotide sequence is at least 95% complementary to its target sequence.

We claim:

1. A method for determining the presence or amount of an RNA sequence in a purified sample containing nucleic acids, the method comprising:
   (a) hybridizing a polynucleotide probe with the RNA sequence in the purified sample, to produce a mixture containing hybridized sequences and single-stranded non-hybridized sequences, wherein the polynucleotide probe comprises
       (1) a sequence which hybridizes to the RNA sequence to be determined, and
       (2) at least two different residues which are chemically or enzymatically bound to the polynucleotide probe, wherein one of the at least two residues is a specifically bindable chemical group which is capable of specifically binding to a specific binding substance and another of the at least two residues is a detectable label;
   (b) thereafter combining the mixture with a cleaving agent which is selective for the single-stranded non-hybridized sequences, to cleave the single-stranded non-hybridized sequences into at least one of mononucleotide and oligonucleotides;
   (c) thereafter contacting the mixture with a solid phase comprising the specific binding substance, and specifically binding the specifically bindable chemical group to the specific binding substance to immobilize the hybridized sequences to the solid phase;
   (d) thereafter separating the mixture and the solid phase having the specifically bound hybridized sequences thereon; and
   (e) thereafter directly or indirectly detecting the detectable label on the specifically bound hybridized sequences or in the mixture, to determine the presence or the amount of the RNA sequence.

2. The method of claim 1, wherein the solid phase is located on an inner surface of a reaction vessel.

3. The method of claim 2, wherein the separating step (d) comprises washing the inner surface of the reaction vessel.

4. The method of claim 1, wherein the specifically bindable chemical group is selected from the group consisting of biotin, iminobiotin and avidin.

5. The method of claim 1, wherein the detectable label is a hapten and the hapten is digoxigenin.

6. The method of claim 1, wherein the specific binding substance of the solid phase is streptavidin or avidin.

7. The method of claim 1, wherein the detecting step (e) comprises directly or indirectly detecting the detectable label in the mixture.

8. The method of claim 1, wherein the detectable label and the specifically bindable chemical group are present on the polynucleotide probe in a ratio of from 10 to 1 to 1 to 1.

9. The method of claim 1, wherein the cleaving agent is at least one agent selected from the group consisting of RNase A, RNase T1 and RNase I, and the combining step (b) comprises incubating the cleaving agent with the mixture for an incubation period of about 2 minutes to 3 hours at a temperature range of about 10° to 80° C.

10. The method of claim 9, wherein the combining step (b) comprises incubating the cleaving agent with the mixture for an incubation period of about 10 minutes to 1 hour at a temperature range of about 20° to 50° C.

11. The method of claim 1, wherein the detectable label is a hapten, and the detecting step (e) comprising incubating the specifically bound hybridized sequences with a labeled antibody which is specific for the hapten to specifically bind the labeled antibody to the hybridized sequences and thereafter detecting the antibody to indirectly detect the detectable label.

12. The method of claim 1, wherein the detecting step (e) comprises directly detecting the detectable label on the specifically bound hybridized sequences.

13. The method of claim 1, wherein the polynucleotide probe is prepared by in vitro transcription from a template nucleic acid, and the at least two different residues are bound to the polynucleotide probe during the in vitro transcription of the polynucleotide probe.

14. A method for determining the presence or amount of an RNA sequence in a sample, comprising:
   (a) combining the sample with a lysis or hybridization buffer;
   (b) hybridizing a polynucleotide probe with the RNA sequence in the sample, to produce a mixture containing hybridized sequences and single-stranded non-hybridized sequences, wherein the polynucleotide probe comprises
      (1) a sequence which hybridizes to the RNA sequence to be determined, and
      (2) at least two different residues which are chemically or enzymatically bound to the polynucleotide probe, wherein one of the at least two residues is a specifically bindable chemical group which is capable of specifically binding to a specific binding substance and another of the at least two residues is a detectable label;
   (c) diluting the mixture formed in step (b) with a sufficient amount of a second buffer such that, in the following step (d), the single-stranded non-hybridized sequences can be cleaved in the presence of the lysis or hybridization buffer;
   (d) thereafter combining the mixture with a cleaving agent which is selective for the single-stranded non-hybridized sequences, to cleave the single-stranded non-hybridized sequences into at least one of mononucleotide and oligonucleotides;
   (e) thereafter contacting the mixture with a solid phase comprising the specific binding substance, and specifically binding the specifically bindable chemical group to the specific binding substance to immobilize the hybridized sequences to the solid phase;
   (f) thereafter separating the mixture and the solid phase having the specifically bound hybridized sequences thereon; and
   (g) thereafter directly or indirectly detecting the detectable label on the specifically bound hybridized sequences or in the mixture, to determining the presence or the amount of the RNA sequence.

15. The method of claim 14, wherein the solid phase is located on an inner surface of a reaction vessel.

16. The method of claim 15, wherein the separating step (f) comprises washing the inner surface of the reaction vessel.

17. The method of claim 14, wherein the specifically bindable chemical group is selected from the group consisting of biotin, iminobiotin and avidin.

18. The method of claim 14, wherein the detectable label is a hapten and the hapten is digoxigenin.

19. The method of claim 14, wherein the specific binding substance of the solid phase is streptavidin or avidin.

20. The method of claim 14, wherein the detecting step (g) comprises directly or indirectly detecting the detectable label in the mixture.

21. The method of claim 14, wherein the detectable label and the specifically bindable chemical group are present on the polynucleotide probe in a ratio of from 10 to 1 to 1 to 1.

22. The method of claim 14, wherein the lysis or hybridization buffer comprises guanidinium thiocyanate and has a maximum of 5% residual activity of RNase.

23. The method of claim 22, wherein the lysis or hybridization buffer further comprises at least one additional ingredient selected from the group consisting of an RNase inhibitor, dimethyldicarbonate and diethylpyrocarbonate.

24. The method of claim 14, wherein in step (c) the mixture is diluted by about 1:2 to 1:100.

25. The method of claim 14, wherein the cleaving agent is at least one agent selected from the group consisting of RNase A, RNase T1 and RNase I, and the combining step (d) comprises incubating the cleaving agent with the mixture for an incubation period of about 2 minutes to 3 hours at a temperature range of about 10° to 80° C.

26. The method of claim 25, wherein the combining step (d) comprises incubating the cleaving agent with the mixture for an incubation period of about 10 minutes to 1 hour at a temperature range of about 20° to 50° C.

27. The method of claim 14, wherein the detectable label is a hapten, and the detecting step (g) comprising incubating the specifically bound hybridized sequences with a labeled antibody which is specific for the hapten to specifically bind the labeled antibody to the hybridized sequences and thereafter detecting the antibody to indirectly detect the detectable label.

28. The method of claim 14, wherein the detecting step (g) comprises directly detecting the detectable label on the specifically bound hybridized sequences.

29. The method of claim 14, wherein the polynucleotide probe is prepared by in vitro transcription from a template nucleic acid, and the at least two different residues are bound to the polynucleotide probe during the in vitro transcription of the polynucleotide probe.

30. A kit for determining the presence or amount of a single-stranded polynucleotide sequence, comprising:
   (a) a polynucleotide probe, comprising a sequence which is complementary to the single-stranded polynucleotide sequence to be determined, wherein at least two different residues are bound to the polynucleotide probe, wherein one of the at least two residues is a specifically bindable chemical group which is capable of specifically binding to a binding substance and another of the at least two residues is a detectable chemical group;
   (b) a cleaving agent capable of cleaving single-stranded polynucleotide sequences into at least one of mononucleotides and oligonucleotides;
   (c) an labelled antibody which is specific for the detectable chemical group; and
   (d) a solid phase comprising a binding substance which is capable of binding the specifically bindable group.

31. The kit of claim 30, wherein the labelled antibody is an enzyme-labelled antibody.

32. The kit of claim 30, wherein the solid phase is located on an inner surface of a reaction vessel.

33. The kit of claim 30, wherein the cleaving agent is at least one agent selected from the group consisting of RNase A, RNase T1 and RNase I.

34. The kit of claim 30, wherein component (c) further comprises a substrate for the enzyme label.

35. The kit of claim 30, further comprising a lysis or hybridization buffer.

36. A method for determining the presence or amount of a polynucleotide sequence in a sample, comprising:
   (a) contacting a sample containing a polynucleotide sequence to be determined with a polynucleotide probe, to hybridize the polynucleotide probe with the polynucleotide sequence, to produce a mixture containing hybridized sequences and single-stranded non-hybridized sequences, wherein the polynucleotide probe comprises
  (1) a sequence which is complementary to the polynucleotide sequence to be determined, and
  (2) at least two different residues which are chemically or enzymatically bound to the polynucleotide probe, wherein one of the at least two residues is a specifically bindable chemical group which is capable of specifically binding to a specific binding substance and another of the at least two residues is a detectable label;
(b) diluting the mixture formed in step (a) by about 1:2 to 1:100;
(c) thereafter combining the mixture with a cleaving agent which is selective for the single-stranded non-hybridized sequences, to cleave the single-stranded non-hybridized sequences into at least one of mononucleotide and oligonucleotides;
(d) thereafter contacting the mixture with a solid phase comprising the specific binding substance, and specifically binding the specifically bindable chemical group to the specific binding substance to immobilize the hybridized sequences to the solid phase;
(e) thereafter separating the mixture and the solid phase having the specifically bound hybridized sequences thereon; and
(f) thereafter directly or indirectly detecting the detectable label on the specifically bound hybridized sequences or in the mixture, to determining the presence or amount of the polynucleotide sequence.

* * * * *